United States Patent [19]
Carmen et al.

[11] Patent Number: 5,769,839
[45] Date of Patent: Jun. 23, 1998

[54] LONG-TERM BLOOD COMPONENTS STORAGE SYSTEM AND METHOD

[75] Inventors: Raleigh A. Carmen, Fullerton; Chi Yong Chong, Placentia, both of Calif.; Randy B. Garcez, Carrboro, N.C.

[73] Assignee: PALL Corporation, East Hills, N.Y.

[21] Appl. No.: 708,899

[22] Filed: Sep. 5, 1996

Related U.S. Application Data

[63] Continuation of Ser. No. 339,482, Nov. 14, 1994, abandoned.

[51] Int. Cl.$^6$ .................................................... A61B 19/00
[52] U.S. Cl. ............................ 604/408; 604/410; 128/898
[58] Field of Search .................................... 604/403–410; 128/898

[56] References Cited

U.S. PATENT DOCUMENTS

| | | |
|---|---|---|
| 4,222,379 | 9/1980 | Smith . |
| 4,301,800 | 11/1981 | Collins . |
| 4,451,259 | 5/1984 | Geissler et al. . |
| 4,585,735 | 4/1986 | Meryman et al. ........................ 435/2 |
| 4,767,541 | 8/1988 | Wisdom . |
| 4,810,378 | 3/1989 | Carmen et al. . |
| 4,943,287 | 7/1990 | Carmen ................................ 604/408 |
| 5,250,303 | 10/1993 | Meryman et al. . |

OTHER PUBLICATIONS

Moody, Ed., et al., "Hepatic Peroxisome (micro body) Proliferation in Rats Fed Plasticizers and Related Compounds", Tox and Appl. Pharmc., 45:497–504 (1978).

Kluwe, Wm., et al., "The Carcinogenicity of Dietary DEHP in Fischer 344 Rats and B6C3F$_1$ Mice," J. Toxicol. Environmental Health, 10:797 (1982).

Russo, J.R., "Packaging Breakthrough Yields Savings for Hospitals", Packaging (Feb., 1986).

Meryman, H.T., et al., "Manipulating Red Cell Intra– and Extracellular pH by Washing", Vox Sang, 60:99–104 (1991).

Meryman, H.T., et al., "Refrigerated Storage of Red Cells Resuspended in ARC Solution at High pH", Vox Sang, 60:88–98 (1991).

Eastman Kodak Company "Ecdel Elastomers", product description (Jul., 1993).

*Primary Examiner*—John G. Weiss
*Assistant Examiner*—Dennis Ruhl
*Attorney, Agent, or Firm*—Leydig, Voit & Mayer, Ltd.

[57] ABSTRACT

System and method for storing packed red blood cells (RBCs) long-term in a non-extractable plastic blood storage bag in a hypotonic cell preservation solution, for subsequent human parenteral introduction of the stored red blood cells. In addition, a blood storage bag that contains a volume of blood product, such as packed red blood cells, that have hemolyzed less than 1% during at least 42 days storage in a non-extractable plastic storage bag containing a volume of hypotonic cell preservation solution.

24 Claims, 1 Drawing Sheet

LONG-TERM BLOOD COMPONENTS STORAGE SYSTEM AND METHOD

This disclosure is a continuation of patent application Ser. No. 08/339,482, filed Nov. 14, 1994, abandoned.

TECHNICAL FIELD

This invention relates generally to biological materials storage systems. More specifically, this invention relates to a system and method for long-term storage of blood components.

BACKGROUND

Red blood cells (RBCs) commonly are separated from whole blood for subsequent infusion into a recipient. The storage of RBCs in containers, primarily plastic blood bags, is a well-known and established practice. The RBCs initially are separated from whole blood in a container (plastic bag) by centrifugation of the collected whole blood. Following centrifugation, which produces a lower, denser RBC portion and an upper, lighter plasma portion, the upper plasma is removed from the container by expressing it from an opening at the upper part of the container. The separated RBCs remaining in the container are referred to as packed RBCs.

Packed RBCs can be stored for relatively long periods if a RBC preservation solution is added to the container, or storage bag. Historically isotonic storage solutions were used to store and preserve RBCs collected for patient infusion. It then was hypothesized that a hypotonic solution would increase the surface tension of cells by osmotic swelling, thus further protecting RBCs during storage.

Storage bags used for long-term storage of RBCs typically now are manufactured using a plastic film comprising polyvinyl chloride (PVC) plasticized with a plasticizer, such as dioctylphthalate (DOP), also known as di-2-ethylhexylphthalate (DEHP), n-butyryl-tri-n-hexyl citrate (B6), trioctyltrimellitate (TOTM), or the like.

One of the early ways to extend the storage time of RBCs in plastic blood bags was based on an observation that certain plasticizer extractants found in conventional blood bag plastic materials tended to have a beneficial effect on RBC storage. Specifically, it was found that when RBCs were stored in a PVC plastic system plasticized with a plasticizer known as DEHP, the extraction of the DEHP into the stored cells somehow facilitated a reduction in hemolysis.

However, the presence of such plasticizer contaminants is undesirable in a product for parental human use. Data suggests that RBC storage in a DEHP plasticized bag at 4° C. over a six week (42 days) period results in about 54 mg/L migrated plasticizer concentration in the RBC product. Similarly, RBC storage in a B6 plasticized bag at the same temperature and duration results in about 51–55 mg/L migrated plasticizer concentration in the RBC product.

Thus, the observed benefit of using plasticized PVC containers to reduce hemolysis of stored RBCs for long periods is mitigated by concerns of plasticizer contamination in a product intended for parenteral use in humans. Not only is it undesirable to transfuse such chemicals into the blood stream of the recipient of such stored packed RBCs, some plasticizers, such as DEHP, are listed as carcinogens in rodents.

Although the exact cause of hemolysis in stored RBCs remains uncertain, it is known that the expression of certain white blood cells (WBC) enzymes may contribute to RBC hemolysis, especially with time. Thus, in an effort to avoid the problem of plasticizer extraction for long term RBC storage, it was found that subjecting the RBCs to a pre-storage leukocyte filtration prior to storage, enables storage of the RBCs in a plasticized bag system.

In many instances it may not be possible to do a pre-storage filtration of RBCs to remove leukocytes prior to storing RBCs in non-extractable plasticizer storage bags. Thus, to obtain long-term RBC storage, it still is necessary to use blood bag plastic materials manufactured using plasticizers which are extractable into the stored RBC product.

Thus, there remains a need for a convenient, cost-effective system and method for long-term storage, preferably at least 42 days, of blood components such as packed RBCs, with minimum plasticizer contamination.

Relevant Literature

U.S. Pat. No. 4,585,735 to Meryman et al., issued 29 Apr. 1986, describes a hypotonic suspension medium and a method for prolonged storage of red blood cells at about 4° C.

U.S. Pat. No. 4,222,379 to Smith, issued 16 Sep. 1980, describes a multiple blood bag system having a donor bag made from certain ester-type plasticizers. That patent discloses that the presence of plasticizers cause a significant lowering of the plasma hemoglobin content during long-term RBC storage, thus, effects longer RBC storage time.

U.S. Pat. No. 4,301,800 to Collins, issued 24 Nov. 1981, describes PVC blood bag inserts that increase the amount of extractable plasticizer that migrates from the blood bag into the stored RBC product. This patent discloses that the presence of extractable plasticizer increases RBC blood storage time.

U.S. Pat. No. 4,451,259 to Geissler et al., issued 29 May 1984, describes storing blood in blood bags made from blood-extractable esters to cause such stored blood that is in contact with the polymer to exhibit a low hemolysis rate.

U.S. Pat. No. 4,943,287 to Carmen, issued 24 Jul. 1990, describes RBCs that are pre-filtered and stored in TOTM plasticized PVC blood bags for up to 42 days. Using blood bags made from that plasticizer results in an extractive level of less than one part per million over a defined period of time. However, that patent discloses that long-term storage in bags made from the non-extractable plasticizer must be pre-filtered prior to storage.

SUMMARY OF THE INVENTION

Quite surprisingly, we now have found that by using a hypotonic red blood cell (RBC) storage solution in combination with a non-extracting plastic blood storage bag, we obtain the benefits of long-term storage, such as at least 42 days, of blood components without the contamination of extractives.

According to the subject invention, a system for long-term storage of a blood product, together with a method for such long-term storage, and a plastic storage bag for such long-term storage, are provided.

The system includes a plastic bag, made substantially free of blood extractable plasticizers, and an amount of a hypotonic biologically compatible buffered cell preservative solution contained within the bag. The plastic bag is made from a plasticizer that releases less than 1 ppm plasticizer into the cell preservative solution during the long-term storage, preferably the plasticizer trioctyltrimellitate. The plastic bag also preferably is made from poly (vinyl chloride), ethylene vinyl acetate, or a copolyester ether.

The plastic bag of the present system also may contain a stored volume of blood product, such as packed red blood cells, having less than about 1% hemolysis after about 42 days of storage. The blood product preferably includes packed red blood cells, or filtered or unfiltered red blood cells.

The present method comprises generally of collecting a sample of the blood product in a plastic blood storage bag that is substantially free of blood extractable plasticizers, the blood bag containing an amount of a hypotonic cell preservative solution. Then, the plastic blood storage bag containing the blood product is stored at a predetermined temperature, preferably at about 4° C., for a time period of about 42 days or more. The method may further include the step of collecting whole blood into a collection bag, filtering the whole blood to substantially remove leukocytes, resulting in a pre-filtered packed red blood cell sample. The pre-filtered packed red blood cells then are transferred into the plastic storage bag for long-term storage.

The invention further includes a blood storage bag that contains a volume of blood product, such as packed red blood cells, that have hemolyzed less than 1% during at least 42 days storage in a non-extractable plastic storage bag containing a volume of hypotonic cell preservation solution.

The invention is described in further detail in the attached claims and in the detailed description below.

Detailed Description of Specific Embodiments

Figure 1:
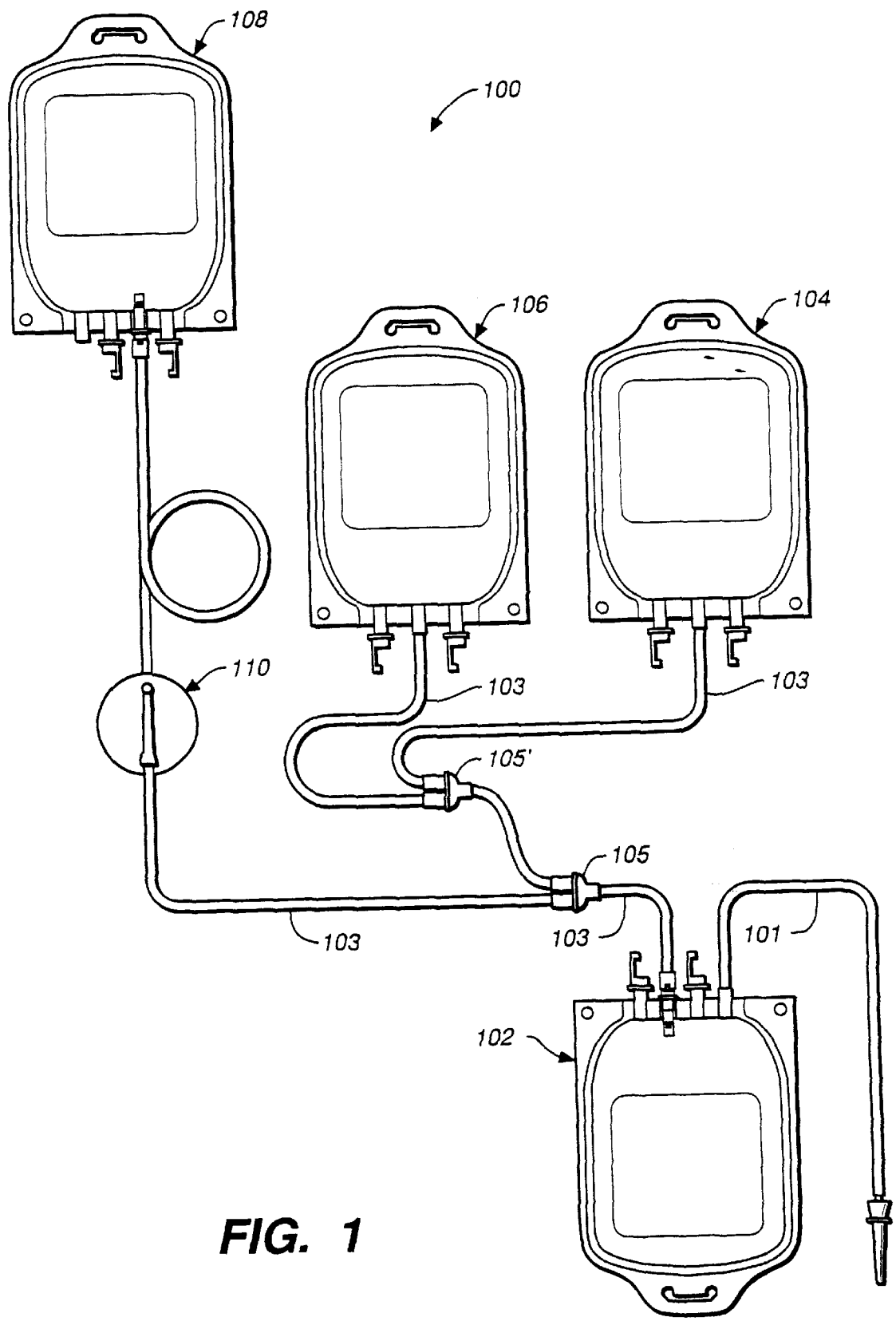
FIG. 1 is a plan view of a multiple blood bag filtering system that may be used with the present invention.

The present invention generally relates to a system and method for storing packed red blood cells (RBCs) long-term for subsequent parenteral introduction into a human.

The Food and Drug Administration (FDA) presently requires a percent hemolysis value of less than one (i.e., <1% hemolysis) for stored blood components, such as red blood cells, that are being reintroduced into a human patient. As indicated above, there has been a long-felt need in the art to find a method for long-term storage of blood components. By long-term typically is meant about 42 days or longer, typically in the range of about 42 days to about 125 days.

Such long-term storage of packed red blood cells has been achieved by storage in plastic bags manufactured using plasticizers that leach into the stored blood. This has an undesirable effect of introducing chemical contaminants into re-infused blood products. Long-term storage of packed red blood cells has been achieved in plastic blood bags made from non-extractable, or non-leachable, plasticizers only when the blood is pre-filtered and stored in an isotonic solution. The isotonicity was considered to be important in assuring preservation of pre-filtered cells.

The present invention surprisingly achieves a one percent (1%) hemolysis value by combining a non-extractable plastic blood bag and a hypotonic cell preservative solution, with or without pre-filtering. The system and method may be used to store blood components, including packed red blood cells (erythrocytes), pre-filtered or non-pre-filtered red blood cells, and possibly other blood components such as platelets and leukocytes.

Plastic blood bags for storing blood components are generally known and commercially available. Most blood bags are manufactured from a base of poly (vinyl chloride), or PVC, while others are manufactured from a base of ethylene vinyl acetate. These blood bags generally are made from a flexible film that can be radio-frequency (RF) or heat sealed to form a bag that withstands rupturing during pressure heat sterilization and high-speed centrifugation. Preferably, the bag transmits carbon dioxide and oxygen.

To achieve the degree of flexibility required for, in particular, PVC bags, the PVC contains a certain percentage of a plasticizer. The plasticizer of the present invention preferably is one that is known to be non-extractable, i.e., it does not leach into stored blood components. A non-extractable plasticizer is defined as one that releases less than 1 ppm of plasticizer into the stored blood component. Such known plasticizers include tri 2-ethylhexyl trimellitate, or trioctyltrimellitate (TOTM). Other non-extractable plasticizers that may be known may be used in practicing the present invention.

In addition, novel non-extractable materials that do not require the addition of a plasticizer may be used to manufacture blood storage bags used in practicing the present invention. Examples of such materials include copolyester ethers, such as poly-cyclohexane-di-methylcyclohexane-di-carboxylate elastomer (PCCE). PCCE is commercially available under the name ECDEL™ elastomer from Eastman Chemical Products, Kingsport, Tenn. Other non-extractable materials having the desired characteristics for storage of blood components, as set forth above and as determined by the FDA and other regulating agencies, may be used in practicing the present invention.

The present invention includes the combination of a plastic blood bag, as described generally above, with a hypotonic biologically compatible buffered cell preservation solution. By hypotonic is meant that the solution includes a biologically compatible buffered solution containing impermeable solutes having an effective osmolality that is hypotonic. The buffering agent may include sodium phosphate, or any known biologically compatible buffers. Impermeable solutes, as used herein, are solutes incapable of freely traversing the cell membrane of cells, such as red blood cells, by passive diffusion.

One aspect of the present invention is that the cell preservative solution is hypotonic. The hypotonic cell preservative solution maintains the stored cells in a slightly distended state. This distended state of the stored blood components, due to the osmolality and has been shown to increase the length of storage for blood cells. (See, U.S. Pat. No. 4,585,735 to Meryman et al.)

Examples of solutions that may be used in practicing the present invention are described in U.S. Pat. No. 5,250,303 and U.S. Pat. No. 4,585,735, both to Meryman et al., both of which are incorporated by reference in their formulations and certain definitions of terms used herein. In addition, modifications of those Meryman et al. formulations are considered to be within the scope of this invention.

In one embodiment, the preservation solutions are substantially free from chloride ions. In addition, the intracellular pH ($pH_i$) to extracellular pH ($pH_x$) differential preferably is maintained during the storage period for long-term storage of blood components. This differential results from the chloride shift and is maintained throughout the storage period as long as penetrating anions are not reintroduced.

Preferably, the ratio of RBC to cell preservative solution is about 2:1, i.e., about 200 ml RBC to about 100 ml preservative solution.

The specific formulation of the hypotonic preservative solution may be modified, so long as the hypotonicity of the final solution is such that the stored cells remain slightly distended due to the osmolality. Specific samples of formulations are found in the Exemplification below.

A formulation of the hypotonic preservative solution of the present invention may include the following components: about 12 to about 25 g/L dextrose; less than about 2.0 g/L anhydrous sodium phosphate; less than about 2.0 g/L disodium phosphate; less than about 2.0 g/L trisodium phosphate; less than about 0.3 g/L adenine; about 1.5 to about 10 g/L trisodium citrate dihydrate; less than about 3.0 g/L sodium gluconate; and less than about 3.0 g/L mannitol, wherein the solution is at about pH 7.0 to about 11.0. An alternative formulation of the hypotonic preservative of the present invention may include the following components: about 12.0 to about 13.0 g/L dextrose; less than about 2.0 g/L anhydrous sodium phosphate; less than about 2.0 g/L disodium phosphate; about 0.2 to about 0.4 g/L adenine; about 5.0 to about 6.0 g/L trisodium citrate dihydrous; about 2.0 to about 3.0 g/L mannitol; and less than about 1.0 g/L citric acid, wherein the solution is at about pH 5.5 to about 9.0.

The present invention may be practiced using a single blood storage bag, or multiple blood storage bags. In one embodiment, the invention is used in conjunction with a closed multiple blood bag system, wherein the storage bag is made using a non-extractable plasticizer and the cell preservative solution is a hypotonic buffered cell preservative solution.

FIG. 1 is a plan view of an example of a multiple blood bag system 100 that may be used in practicing the present invention. As illustrated, the system 100 includes a whole blood collection bag 102 in continuous closed communication via plastic tubing 103 with satellite bags 104 and 106 via typical Y-connectors 105, 105'. The satellite bags 104, 106 may be used to capture various blood components or to hold various blood additives.

In practicing an embodiment of the invention, whole blood is collected via tubing 101 from a donor into collection bag 102, which typically contains an anticoagulant solution. The whole blood then is centrifuged using normal procedures (e.g., 3000 rpm for 2 minutes) to separate the whole blood into denser packed red blood cells and less dense platelet rich plasma. By opening a conventional valve (not shown) between donor bag 102 and one of the satellite bags 104, 106, the platelet-rich plasma may be expressed into one of the satellite bags by known means (e.g., by using a plasma expresser), leaving behind the packed red blood cells in donor bag 102.

The packed red blood cells (RBCs) include both white blood cells (WBCs) and some platelets, both of which may be removed by commercially available leukocyte filters. Such a filter, when used, may be introduced at, for example, location 110 identified in FIG. 1. Filters suitable for use in this system are generally commercially available under the RC™ series from the Pall Corporation, East Hills, N.Y.

In another embodiment of the present invention, the packed RBCs containing the WBCs and the platelets may be transferred directly into the storage bag 108 without passing through a filter.

The packed red blood cells are transferred from the donor bag 102 into the blood storage bag 108, which is of the type described above, and which is made using a non-extractable plasticizer or made from a non-extractable material. The blood storage bag 108 preferably contains an amount of a hypotonic cell preservative solution, with which the packed red blood cells come in contact during long-term storage.

In one embodiment, the hypotonic cell preservative solution may be contained within one of the satellite bags 104, 106 for introduction into the storage bag 108 upon or prior to transfer of the packed red blood cells into that bag.

In another embodiment, the donor bag 102 may be made using a non-extractable plasticizer, and that bag 102 may also be used as the blood storage bag for long-term blood component storage. In that embodiment, the hypotonic cell preservative solution may be introduced from one of the satellite bags 104, 106 into the donor bag 102 prior to or after whole blood collection. Alternatively, after whole blood is collected into the donor bag 102, the bag may be centrifuged, as described above, and selected blood components may be removed prior to introduction of the hypotonic cell preservative solution into the bag 102 and prior to long-term storage.

The present invention is further described in the following non-limiting examples.

EXEMPLIFICATION

EXAMPLE 1

TOTM Non-extractable plastic blood storage bag

An examples of a TOTM plastic blood bag is disclosed in U.S. Pat. No. 4,280,497 to Warner et al., and which is owned by the assignee of the present application. As described in that patent, a film from which a blood storage bag may be manufactured may contain about 30 to about 50, preferably about 37 percent weight percent, of TOTM and about 3 to 5, preferably about 3.7 weight percent of a heat stabilization system suitable for medical grade PVC plastics. Such a heat stabilization system may include epoxidized vegetable oils, such as epoxidized soy bean oil and epoxidized linseed oil.

In a preferred embodiment, the plastic blood bag is about 100 parts by weight of PVC homopolymer (medium molecular weight), preferably about 63 parts by weight of tri 2-ethylhexyl trimellitate (TOTM), and about 5 parts by weight of epoxidized soybean oil, all of which are commercially available. These ingredients may be suitably mixed by a blender and formed into sheets by conventional methods, such as by calendaring or by extrusion to a thickness of about 0.015 inch. Blood bags made using this material may be formed using RF or heat sealing techniques known in the art.

Such a bag is commercially available under the name CLX® from Miles Inc., Covina, Calif.

EXAMPLE 2

ECDEL copolyester ether storage bag

Another example of a blood storage bag is manufactured from copolyester ethers (COPE), such as those marketed by Eastman Chemical Products, Kingsport, Tenn., and as sold by that company under the name ECDEL™. These ethers are formed into films having the characteristics necessary for blood bag manufacture, but do not contain a blood extractable component known to contaminate blood products stored within bags manufactured from the films.

EXAMPLE 3

Cell preservative solution I

An example of a hypotonic cell preservative solution that may be used in practicing the present invention has the formula found in the following Table I:

TABLE I

| Chemical | grams/liter |
| --- | --- |
| Dextrose | 24.9 |
| $NaH_2PO_4$—$H_2O$ | 0.40 |
| $Na_2HPO_4$ | 1.70 |
| Adenine | 0.27 |
| $Na_3$ citrate $2H_2O$ | 9.79 |
| effective osmolality (mOsm/L) | 132 |
| total osmolality (mOsm/L) | 274 |

The pH of this solution typically is maintained at about 7.4. This formulation is anticipated as being capable of modification, so long as the hypotonicity of the solution is retained.

EXAMPLE 4
Cell preservative solution II

Another example of a formulation for a hypotonic cell preservative solution that may be used in practicing the present invention is found in the following Table II:

TABLE II

| Chemical | grams/liter |
| --- | --- |
| Dextrose | 12.4 |
| $Na_3PO_4$ | 2.13 |
| Adenine | 0.14 |
| $Na_3$ citrate $2H_2O$ | 2.00 |
| Na gluconate | 3.01 |
| Mannitol | 2.51 |
| effective osmolality (mOsm/L) | 106 |
| total osmolality (mOsm/L) | 174 |

The pH of this solution typically is maintained at about 11.0, to maintain the 2,3-diphosphoglycerate level. Variations of this formula may be possible, so long as the hypotonicity of the resulting solution is retained.

EXAMPLE 5
Cell preservative solution III

Another hypotonic cell preservative solution that may be used in conjunction with the present invention has the formula found in the following Table III:

TABLE III

| Chemical | grams/liter |
| --- | --- |
| Dextrose | 12.4 |
| $Na_2HPO_4$ | 1.85 |
| Adenine | 0.30 |
| $Na_3$ citrate $2H_2O$ | 5.21 |
| Mannitol | 2.51 |
| effective osmolality (mOsm/L) | 111 |
| total osmolality (mOsm/L) | 195 |

The pH of this solution typically is maintained at about 8.7, with an effective osmolality of about 111, and a total osmolality of about 195. Variations of this formula may be used in practicing the present invention, so long as the hypotonicity of the resulting solution is retained.

Storing packed red blood cells in the non-extracting plastic blood bag of Example 1, with pre-filtering leukocytes from the red blood cells prior to storage, containing a volume of Example 5 cell preservative solution, results in the data presented below in Table IV.

The experimental protocol used in generating these data is as follows. The blood bag configuration shown in FIG. 1 may be used in practicing the embodiment of this EXAMPLE 5.

Six units of whole blood are drawn into a blood collection bag containing an anticoagulant solution. The filters preferably are sterily replaced, then The system is permitted to rest two hours at room temperature. The blood bag then is centrifuged for 3 minutes, 44 seconds. Platelet rich plasma is removed, preferably by expression from the collection bag, and the filter is primed using preferably about 100 ml of the cell preservation solution, preferably the Example 5 formulation. The blood is filtered as it is transferred from the collection bag into a storage bag. The resulting packed red blood cells contained in the storage bag are stored for 42 days at 4° C., then tested for percent hemolysis.

TABLE IV

| Unit # | % Hemolysis (Week 0) | % Hemolysis (Week 6) |
| --- | --- | --- |
| 1 | 0.04 | 0.29 |
| 2 | 0.08 | 0.41 |
| 3 | 0.03 | 0.23 |
| 4 | 0.03 | 0.31 |
| 5 | 0.15 | 0.21 |
| 6 | 0.14 | 0.28 |
| Mean | 0.08 | 0.29 |
| Std. Dev. | 0.05 | 0.07 |

These data suggest that the combination of a non-extractable plastic blood storage bag with a hypotonic cell preservation of the type specified, results in a long-term storage, i.e., at least 42 days, of pre-filtered, packed red blood cells with less than 1% hemolysis.

EXAMPLE 6
Cell preservation solution IV.

Another example of a hypotonic cell preservative solution that may be used in practicing the present invention has the formula found in the following Table V:

TABLE V

| Chemical | grams/liter |
| --- | --- |
| Dextrose (anhydrous) | 12.4 |
| $NaH_2PO_4$—$H_2O$ | 1.79 |
| Adenine | 0.30 |
| $Na_3$ citrate $2H_2O$ | 5.21 |
| Mannitol | 2.51 |
| Citric acid (anhydrous) | 0.58 |
| effective osmolality (mOsm/L) | 101 |
| total osmolality (mOsm/L) | 185 |

The pH of this solution typically is maintained at about 5.8, to prevent glucose degradation. Variations on this formulation may be used in practicing the present invention, so long as the hypotonicity of the resulting solution is retained.

Storing packed red blood cells in the non-extracting plastic blood bag of Example 1, with pre-filtering leukocytes from the red blood cells prior to storage, containing a volume of Example 6 cell preservative solution results in the data presented below in Table VI.

The experimental protocol used in generating these data is as follows. As in the above example, the blood bag configuration shown in FIG. 1 may be used in practicing this the embodiment of this Example 6.

Six units of whole blood are drawn into a blood collection bag containing an anticoagulant solution. The filters, which may be the same filters described in the above Example 5, preferably are sterily replaced, then the system is permitted to rest two hours at room temperature. The blood bag then is centrifuged at 2820 RPM for 3 minutes, 44 seconds.

Platelet rich plasma is removed, preferably by expression from the collection bag, and the filter is primed using preferably about 100 ml of the cell preservation solution, preferably the Example 6 formulation. The blood is filtered as it is transferred from the collection bag into a storage bag The resulting packed red blood cells contained in the storage bag are stored for 42 days at 4° C., then tested for percent hemolysis.

TABLE VI

| Unit # | % Hemolysis (Week 0) | % Hemolysis (Week 6) |
|---|---|---|
| 1 | 0.09 | 0.23 |
| 2 | 0.19 | 0.30 |
| 3 | 0.11 | 0.19 |
| 4 | 0.19 | 0.58 |
| 5 | 0.05 | 0.21 |
| 6 | 0.08 | 1.05 |
| Mean | 0.12 | 0.43 |
| Std. Dev. | 0.06 | 0.34 |

These data suggests that the combination of a non-extractable plastic blood storage bag with a hypotonic cell preservation of the type specified, results in a long-term storage, i.e., at least 42 days, of pre-filtered, packed red blood cells with a mean hemolysis of less than one percent.

EXAMPLE 7

No pre-filtering of stored blood components

For this example, blood components were processed as described in the above Example 6, except the pre-filter step was omitted. Thus, the whole blood was collected, and packed red blood cells were obtained. The packed cells then were stored in a non-extracting plastic bag as described in Example 1, containing an amount, preferably about 100 ml, of the cell preservation of Example 6. The packed red blood cells were not filtered prior to long-term storage in the cell preservation solution.

The following hemolysis data were generated in using such a system and method:

TABLE VII

| Unit # | % Hemolysis (Week 0) | % Hemolysis (Week 6) |
|---|---|---|
| 1 | 0.07 | 1.14 |
| 2 | 0.04 | 0.56 |
| 3 | 0.11 | 0.93 |
| 4 | 0.12 | 0.37 |
| 5 | 0.07 | 0.76 |
| 6 | 0.05 | 0.62 |
| Mean | 0.08 | 0.73 |
| Std. Dev. | 0.03 | 0.28 |

These data suggests that the combination of a non-extractable plastic blood storage bag with a hypotonic cell preservation of the type specified, without pre-filtration, results in a long-term storage, i.e., at least 42 days of packed red blood cells with a mean hemolysis of less than one percent.

EXAMPLE 8

Pre-filtered blood components.

Another study was conducted using the non-extracting plastic blood storage bag of Example 2 in combination with the cell preservation solution of Example 5, together with pre-filtration. The protocol outlined in Example 5 was used for this example, with the substitution of the plastic bag of Example 2. The hemolysis data resulting from the study are as follows:

TABLE VIII

| Unit # | % Hemolysis (Week 0) | % Hemolysis (Week 6) |
|---|---|---|
| 1 | 0.07 | 0.36 |
| 2 | 0.07 | 0.94 |
| 3 | 0.09 | 0.41 |
| 4 | 0.15 | 0.44 |
| 5 | 0.10 | 0.22 |
| Mean | 0.10 | 0.47 |
| Std. Dev. | 0.03 | 0.27 |

These data suggest that the combination of a non-extractable plastic blood storage bag with a hypotonic cell preservation of the type specified, results in a long-term storage, i.e., at least 42 days of pre-filtered packed red blood cells with a mean hemolysis of less than one percent.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will readily be apparent to those of ordinary skill in the art in light of the teachings of this invention that certain changes and modifications may be made thereto without departing from the spirit or scope of the appended claims.

What is claimed is:

1. A system for storing a blood product, the system comprising:

a plastic bag substantially free of blood extractable plasticizers; and an amount of a hypotonic biologically compatible buffered cell preservative solution contained in the plastic bag, wherein said preservative solution comprises:
dextrose;
anhydrous sodium phosphate;
disodium phosphate;
trisodium phosphate;
adenine;
trisodium citrate dihydrate;
sodium gluconate; and
mannitol,
wherein the solution is at about pH 7.0 to about 11.0.

2. The system of claim 1, wherein the plastic bag is made with a plasticizer that releases less than 1 ppm plasticizer into the cell preservative solution during long-term storage.

3. The system of claim 1, further comprising a stored volume of an unfiltered blood product in the plastic bag, wherein the stored volume has less than about 1% hemolysis after about 42 days in the plastic bag.

4. The system of claim 1, wherein the blood product is packed red blood cells.

5. The system of claim 1, wherein the plastic bag is made from one from the group consisting of polyvinyl chloride, ethylene vinyl acetate, and a copolyester ether.

6. The system of claim 1, wherein the plasticizer comprises trioctyltrimellitate.

7. The system of claim 1, wherein the system is a closed multiple blood bag system.

8. The system of claim 1 wherein the preservative solution comprises:

greater than about 12 and less than about 25 g/L dextrose;

greater than 0 and less than, about 2.0 g/L anhydrous sodium phosphate;

greater than 0 and less than about 2.0 g/L disodium phosphate;

greater than 0 and less than about 2.0 g/L trisodium phosphate;

greater than 0 and less than about 0.3 g/L adenine;

about 1.5 to about 10 g/L trisodium citrate dihydrate;

greater than 0 and less than about 3.0 g/L sodium gluconate; and greater than 0 and less than about 3.0 g/L mannitol.

9. A method for storing a blood product, comprising:

A. contacting a blood product in a plastic blood storage bag that is substantially free of blood extractable plasticizers with an amount of a hypotonic cell preservative solution, said preservative solution comprising:
dextrose;
anhydrous sodium phosphate;
disodium phosphate;
trisodium phosphate;
adenine;
trisodium citrate dihydrate;
sodium gluconate; and
mannitol,
wherein the solution is at about pH 7.0 to about 11.0; and B. storing the blood product with the cell preservative solution in the plastic blood storage bag.

10. The method of claim 9, wherein the plastic blood storage bag is made with a plasticizer that releases less than 1 ppm plasticizer into the stored blood product.

11. The method of claim 9, wherein a sample of the blood product has less than about 1% hemolysis.

12. The method of claim 9, wherein the plastic bag is made from one from the group of plastics consisting of polyvinyl chloride, ethylene vinyl acetate, and a copolyester ether.

13. The method of claim 9, wherein the plasticizer comprises trioctyltrimellitate.

14. The method of claim 9, carried out in a closed system.

15. The method of claim 9 wherein the preservative solution comprises:

greater than about 12 and less than about 25 g/L dextrose;

greater than 0 and less than about 2.0 g/L anhydrous sodium phosphate;

greater than 0 and less than about 2.0 g/L disodium phosphate;

greater than 0 and less than about 2.0 g/L trisodium phosphate;

greater than 0 and less than about 0.3 g/L adenine;

about 1.5 to about 10 g/L trisodium citrate dihydrate;

greater than 0 and less than about 3.0 g/L sodium gluconate; and greater than 0 and less than about 3.0 g/L mannitol.

16. The method of claim 9 wherein the blood product comprises an unfiltered blood product.

17. A system for storing a blood product, the system comprising:

a plastic bag substantially free of blood extractable plasticizers; and an amount of a hypotonic biologically compatible buffered cell preservative solution contained in the plastic bag, wherein said solution comprises:
dextrose;
anhydrous sodium phosphate;
disodium phosphate;
adenine;
trisodium citrate dihydrate;
mannitol; and
citric acid,
wherein the solution is at about pH 5.5 to about 9.0.

18. The system of claim 17, wherein the plastic bag is made from one from the group consisting of polyvinyl chloride, ethylene vinyl acetate, and a copolyester ether.

19. The system of claim 17, wherein the plasticizer comprises trioctyltrimellitate.

20. The system of claim 17, wherein the system is a closed multiple blood bag system.

21. The system of claim 17 wherein the preservative solution comprises:

about 12 to about 13 g/L dextrose;

greater than 0 and less than about 2.0 g/L anhydrous sodium phosphate;

greater than 0 and less than about 2.0 g/L disodium phosphate;

about 0.2 to about 0.4 g/L adenine;

about 5.0 to about 6.0 g/L trisodium citrate dihydrate;

about 2.0 to less than about 3.0 g/L mannitol; and greater than 0 and less than about 1.0 g/L citric acid.

22. A method for storing a blood product, comprising:

contacting a blood product in a plastic blood storage bag that is substantially free of blood extractable plasticizers with an amount of a hypotonic cell preservative solution, said preservative solution comprising:
dextrose;
anhydrous sodium phosphate;
disodium phosphate;
adenine;
trisodium citrate dihydrate;
mannitol; and
citric acid,
wherein the solution is at about pH 5.5 to about 9.0.

23. The method of claim 22, carried out in a closed system.

24. The method of claim 22 wherein the preservative solution comprises:

about 12 to about 13 g/L dextrose;

greater than 0 and less than about 2.0 g/L anhydrous sodium phosphate;

greater than 0 and less than about 2.0 g/L disodium phosphate;

about 0.2 to about 0.4 g/L adenine;

about 5.0 to about 6.0 g/L trisodium citrate dihydrate;

about 2.0 to less than about 3.0 g/L mannitol; and greater than 0 and less than about 1.0 g/L citric acid.

* * * * *